(12) United States Patent
Endo et al.

(10) Patent No.: US 6,924,272 B2
(45) Date of Patent: Aug. 2, 2005

(54) MEDICINAL COMPOSITION FOR DIABETIC NEUROPATHY

(75) Inventors: Kazuki Endo, Narita (JP); Toichi Abiru, Sawara (JP); Junzo Kamei, Yokohama (JP)

(73) Assignee: Yamasa Corporation, Chiba (JP)

( * ) Notice: Subject to any disclaimer, the term of this patent is extended or adjusted under 35 U.S.C. 154(b) by 39 days.

(21) Appl. No.: 10/381,716

(22) PCT Filed: Sep. 3, 2002

(86) PCT No.: PCT/JP02/08916
§ 371 (c)(1),
(2), (4) Date: Mar. 28, 2003

(87) PCT Pub. No.: WO03/022290
PCT Pub. Date: Mar. 20, 2003

(65) Prior Publication Data
US 2004/0014711 A1 Jan. 22, 2004

(30) Foreign Application Priority Data
Sep. 5, 2001 (JP) .......... 2001-268156
Nov. 6, 2001 (JP) .......... 2001-340838

(51) Int. Cl.[7] .......... A61K 31/70; C07H 19/06
(52) U.S. Cl. .......... 514/51; 514/50; 514/49; 536/28.5
(58) Field of Search .......... 536/28.5, 23; 514/51, 514/50, 49

(56) References Cited
U.S. PATENT DOCUMENTS
4,789,666 A * 12/1988 Gennari .......... 514/51

FOREIGN PATENT DOCUMENTS

| JP | 62-16497 | 1/1987 |
| JP | 2000-044472 | 2/2000 |
| WO | 89/03837 | 5/1989 |
| WO | 99/33476 | 7/1999 |
| WO | 00/11952 | 3/2000 |

OTHER PUBLICATIONS

Lopez et al., J. Nutr. Biochem., vol. 3(6), pp. 313–315, 1992 (abstract provided).*

M. Ohsawa et al., "Possible Involvement of Spinal Protein Kinase C in Thermal Allodynia and Hyperalgesia in Diabetic Mice", European Journal of Pharmacology, 372, pp. 221–228, 1999.

J. Secades et al., "CDP–Choline: Pharmacological and Clinical Review", Methods Find Exp. Clinical Pharmacol., vol. 17, Suppl. B, pp. 1–54, 1995.

* cited by examiner

Primary Examiner—James O. Wilson
Assistant Examiner—Howard V. Owens
(74) Attorney, Agent, or Firm—Wenderoth, Lind & Ponack, L.L.P.

(57) ABSTRACT

The present invention relates to an agent for the prophylaxis or treatment of diabetic neuropathy, which contains cytidine 5'-diphosphocholine (CDP-choline) as an active ingredient. The agent for the prophylaxis or treatment of diabetic neuropathy of the present invention is effective for neuropathy mainly caused by metabolic disturbance of carbohydrate and is also superior in safety. Neuropathy includes peripheral neuropathy and dysautonomia. CDP-choline is effective even by oral administration.

5 Claims, 3 Drawing Sheets

MEDICINAL COMPOSITION FOR DIABETIC NEUROPATHY

This application is a U.S. national stage of International Application No. PCT/JP02/08916 filed Sep. 3, 2002.

TECHNICAL FIELD TO WHICH THE INVENTION PERTAINS

The present invention relates to an agent for the prophylaxis or treatment of diabetic neuropathy containing cytidine 5'-diphosphocholine (CDP-choline) as an active ingredient, a method for the prophylaxis or treatment of said disorder, comprising administering an effective amount of CDP-choline, use of CDP-choline for the production of a pharmaceutical agent for the prophylaxis or treatment of said disorder, and a pharmaceutical composition for the prophylaxis or treatment of said disorder comprising an effective amount of CDP-choline and a pharmaceutically acceptable carrier.

BACKGROUND ART

At present, treatments of diabetes are symptomatic and rely on administration of insulin or hypoglycemic agents. However, a long-term control of blood sugar is difficult, not to mention complete cure of diabetes, and in case of longer period of the disease, more diversified complications are induced. Of such complications, a general disease state of diabetic peripheral neuropathy is bilaterally symmetrical and sensory nerve dominant polyneuropathy. In acute symptoms, excitement of nerves such as sensory abnormality, allodynia (to feel pain by light touch of body surface) and the like is observed, and in chronic symptoms, diminished sensation (limb numbness, cold sense etc.), pain and the like are observed. In addition, diabetic dysautonomia is mainly developed in diabetic patients having polyneuropathy, thus putting every organ under control of autonomic nerve at risk for abnormality, and abnormal bowel movement such as constipation and diarrhea, impotence, orthostatic hypotension, dyshidrosis, gastric emptying delay and the like are observed.

For diabetic neuropathy showing such diversified symptoms, epalrestat (manufactured by Ono Pharmaceutical Co., Ltd.), which is an aldose reductase inhibitor, has been approved and used only in Japan. However, various problems have been pointed out as regards efficacy and side effects of this drug [The Informed Prescriber, vol. 11, pages 122 and 125, December (1996)]. Moreover, mexiletine hydrochloride (manufactured by Nippon Boehringer Ingelheim Co., Ltd.), which has been used as a therapeutic drug for tachyarrhythmia (ventricular), has been additionally approved and used for efficacy and effect in improvement of subjective symptoms (spontaneous pain, numbness) of diabetic neuropathy. However, its spontaneous pain relieving rate is not more than 50%, as reported in the Phase III—controlled clinical trial—, and the drug is not entirely satisfactory as a therapeutic agent for diabetic neuropathy.

The main purpose in present-day therapy of diabetes is to prevent the onset and progress of diabetic complications, and the development of a drug for diabetic complications, which shows a high therapeutic effect and a high safety, is desired.

Under the circumstances, in a connection between nucleic acid related compounds and neuropathy, it has been reported that triacetyluridine is effective for peripheral neuropathy (diminished sensation) induced by taxol, which is an anticancer agent [WO 00/11952].

However, peripheral neuropathy induced by taxol, which is an anticancer agent, and diabetic neuropathy are completely different diseases in causes of onset. In addition, the above international publication does not consider or even suggest whether or not triacetyluridine is effective for neuropathy derived from metabolic disturbance of carbohydrate, namely, diabetic neuropathy. Moreover, the above international publication exemplarily indicates CDP-choline, other than triacetyluridine, as an active ingredient. However, CDP-choline is merely shown as an example in the above international publication, without any specific data, much less a description or data relating to the effect of CDP-choline on diabetic neuropathy.

DISCLOSURE OF THE INVENTION

In view of the above situation, the present inventors have intensively studied the efficacy of nucleic acid related compounds on diabetic neuropathy and found that, while having been conventionally permitted for use only by intravenous administration for the application to disorders in the central nerve system, such as consciousness disorder associated with head injury and brain operation, CDP-choline surprisingly shows, by oral administration, a superior improving effect on the symptoms observed in diabetic peripheral neuropathy, such as sensory abnormality and the like, and on the symptoms derived from diabetic dysautonomia, such as degraded transportability of gastrointestinal tract and the like, thereby achieving the present invention.

Accordingly, the present invention provides the following.
(1) An agent for the prophylaxis or treatment of diabetic neuropathy, which comprises CDP-choline or a pharmaceutically acceptable salt thereof as an active ingredient.
(2) The agent for the prophylaxis or treatment of diabetic neuropathy of the above (1), wherein the diabetic neuropathy is a neuropathy mainly caused by metabolic disturbance of carbohydrate.
(3) The agent for the prophylaxis or treatment of diabetic neuropathy of the above (1), wherein the diabetic neuropathy is a peripheral neuropathy.
(4) The agent for the prophylaxis or treatment of diabetic neuropathy of the above (1), wherein the diabetic neuropathy is dysautonomia.
(5) The agent for the prophylaxis or treatment of diabetic neuropathy of any of the above (1)–(4), which is in a dosage form for oral administration.
(6) A method for the prophylaxis or treatment of diabetic neuropathy, which comprises administering an effective amount of CDP-choline or a pharmaceutically acceptable salt thereof.
(7) The method of the above (6), wherein the diabetic neuropathy is a neuropathy mainly caused by metabolic disturbance of carbohydrate.
(8) The method of the above (6), wherein the diabetic neuropathy is peripheral neuropathy.
(9) The method of the above (6), wherein the diabetic neuropathy is dysautonomia.
(10) The method of any of the above (6)–(9), which comprises oral administration.
(11) Use of CDP-choline or a pharmaceutically acceptable salt thereof for the production of a pharmaceutical agent for the prophylaxis or treatment of diabetic neuropathy.
(12) The use of the above (11), wherein the diabetic neuropathy is a neuropathy mainly caused by metabolic disturbance of carbohydrate.
(13) The use of the above (11), wherein the diabetic neuropathy is a peripheral neuropathy.

(14) The use of the above (11), wherein the diabetic neuropathy is dysautonomia.

(15) The use of any of the above (11)–(14), wherein the pharmaceutical agent for the prophylaxis or treatment is in a dosage form for oral administration.

(16) A pharmaceutical composition for the prophylaxis or treatment of diabetic neuropathy, which comprises an effective amount of CDP-choline or a pharmaceutically acceptable salt thereof, and a pharmaceutically acceptable carrier.

(17) The pharmaceutical composition of the above (16), wherein the diabetic neuropathy is a neuropathy mainly caused by metabolic disturbance of carbohydrate.

(18) The pharmaceutical composition of the above (16), wherein the diabetic neuropathy is a peripheral neuropathy.

(19) The pharmaceutical composition of the above (16), wherein the diabetic neuropathy is dysautonomia.

(20) The pharmaceutical composition of any of the above (16)–(19), which is in a dosage form for oral administration.

(21) A commercial package comprising the pharmaceutical composition of any of the above (16)–(20) and a written matter associated therewith, the written matter stating that the pharmaceutical composition can or should be used for the prophylaxis or treatment of diabetic neuropathy.

BEST MODE FOR EMBODYING THE INVENTION

Figure 1:
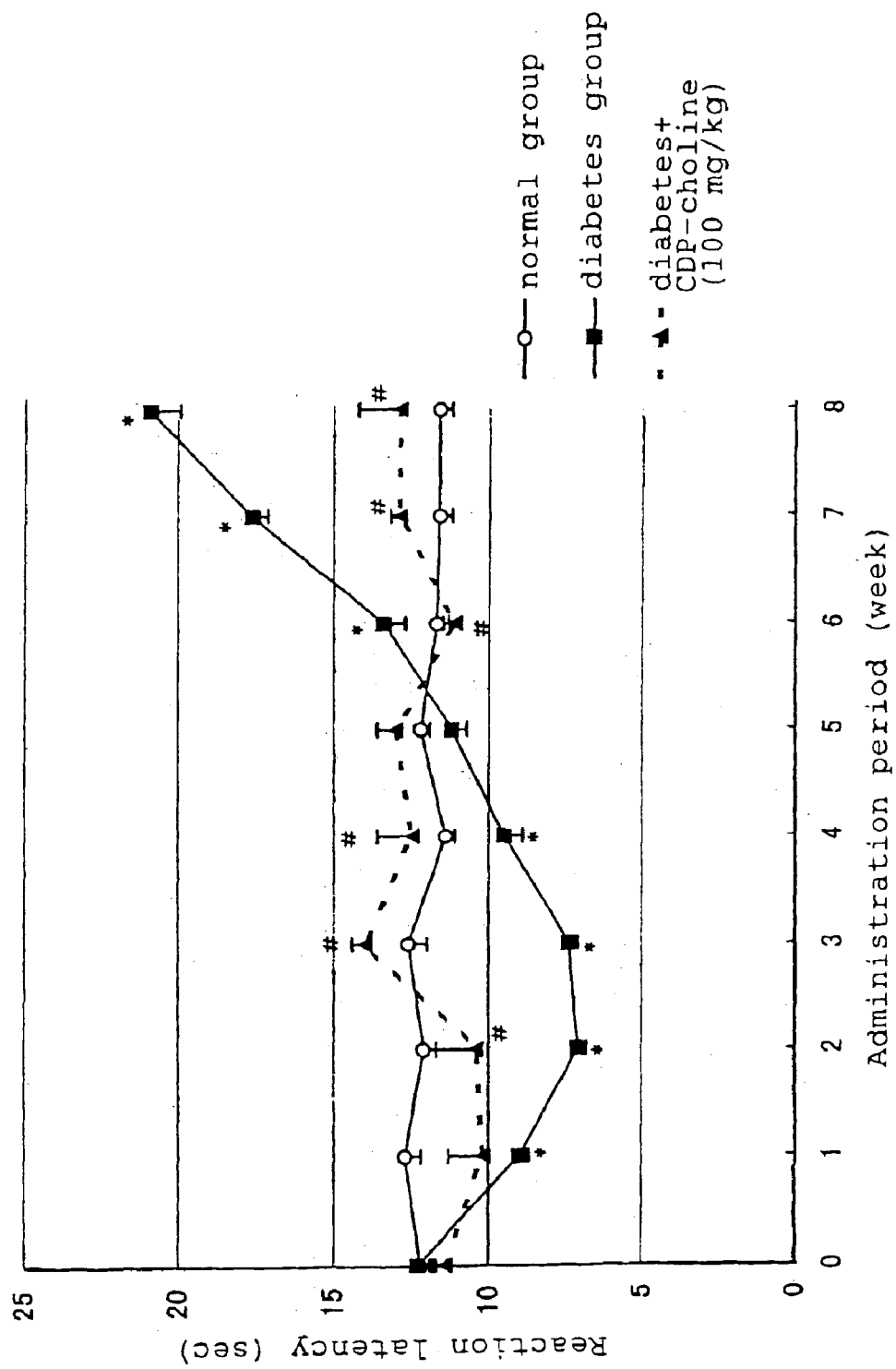
FIG. 1 shows the results of CDP-choline regarding assessment (threshold analysis) of thermal nociceptive response, wherein the longitudinal axis shows reaction latency (sec), and the transverse axis shows administration period (weeks) of CDP-choline.

The present invention provides an agent for the prophylaxis or treatment of diabetic neuropathy, which comprises CDP-choline or a pharmaceutically acceptable salt thereof as an active ingredient.

The present invention also provides a method for the prophylaxis or treatment of diabetic neuropathy, which comprises administering an effective amount of CDP-choline or a pharmaceutically acceptable salt thereof.

The present invention further provides use of CDP-choline or a pharmaceutically acceptable salt thereof for the production of a pharmaceutical agent for the prophylaxis or treatment of diabetic neuropathy.

The present invention moreover provides a pharmaceutical composition for the prophylaxis or treatment of diabetic neuropathy, which comprises an effective amount of CDP-choline or a pharmaceutically acceptable salt thereof, and a pharmaceutically acceptable carrier, and a commercial package comprising said pharmaceutical composition and a written matter relating to the pharmaceutical composition.

CDP-choline and a pharmaceutically acceptable salt thereof are effective for the prophylaxis or treatment of diabetic neuropathy, specifically neuropathy mainly caused by metabolic disturbance of carbohydrate. Such neuropathy includes peripheral neuropathy and dysautonomia, wherein the general disease state of peripheral neuropathy is bilaterally symmetrical and sensory nerve dominant polyneuropathy. The classification, designation and the like of neuropathy in the present specification are in accordance with The Merck Manual 17th Edition.

According to the present invention, for example, it is possible to inhibit the onset of both the symptoms in acute state (sensory abnormality, allodynia and the like) and the symptoms in chronic state (limb numbness, cold sense, pain and the like), or improve such symptoms after the onset thereof, by administering CDP-choline or a pharmaceutically acceptable salt thereof to a diabetic patient before development of the symptoms specific to peripheral neuropathy or after the onset thereof. Furthermore, it is possible to inhibit the onset of the symptoms specific to dysautonomia, such as abnormal bowel movement, gastric emptying delay and the like due to degraded transportability of gastrointestinal tract, or improve such symptoms after the onset thereof, by administering CDP-choline to a diabetic patient before development of the symptoms specific to dysautonomia or after the onset thereof.

CDP-choline may be in a free form or a salt form as an active ingredient of an agent or a pharmaceutical composition for the prophylaxis or treatment of diabetic neuropathy of the present invention. Examples of the salt form include, but not limited to, alkali metal salts such as lithium salt, sodium salt, potassium salt and the like; alkaline earth metal salts such as magnesium salt and the like; and the like. Of these, a pharmaceutically acceptable salt is particularly preferable.

CDP-choline and a salt thereof may be a hydrate or a solvate. In the case of a hydrate, a hydrate or a salt hydrate wherein 1–20 molecules of water is(are) adhered or bonded to 1 molecule of CDP-choline or a salt thereof, is exemplified.

Furthermore, CDP-choline and a salt thereof, and a hydrate or a salt hydrate thereof (hereinafter to be simply referred to as CDP-choline) in the form of a crystal or a noncrystal can be used in the present invention.

Such CDP-choline is a known compound, and can be obtained as a commercially available product or can be produced according to a known method (see JP-A-6-31306, EP Patent No. 329627, U.S. Pat. No. 6,057,301 and the like).

CDP-choline is effective for the prophylaxis or treatment of the above diabetic neuropathy by any of oral administration, parenteral administration, intrarectal administration and local administration.

The agent or pharmaceutical composition for the prophylaxis or treatment of diabetic neuropathy of the present invention can be prepared by mixing the aforementioned CDP-choline and a conventional carrier for preparation and processing the mixture into a preparation. The content of CDP-choline in the preparation or composition may be appropriately determined from the range of not less than 0.01% (w/w), preferably 1–80% (w/w).

As a carrier for the preparation, a substance conventionally used in the field of preparations, which does not react with CDP-choline, is used. Specific examples include lactose, glucose, mannitol, dextrin, starch, sucrose, magnesium aluminometasilicate, synthetic aluminum silicate, crystalline cellulose, carboxymethylcellulose sodium, hydroxypropylstarch, carboxymethylcellulose calcium, ion exchange resin, methylcellulose, gelatin, gum arabic, hydroxypropylcellulose, low-substituted hydroxypropylcellulose, hydroxypropylmethylcellulose, polyvinylpyrrolidone, polyvinyl alcohol, light anhydrous silicic acid, magnesium stearate, talc, carboxy vinyl polymer, titanium oxide, sorbitan fatty acid ester, sodium lauryl sulfate, glycerine, fatty acid glycerine ester, purified lanolin, glycerinated gelatin, polysorbate, macrogol, vegetable oil, wax, liquid paraffin, white petrolatum, nonionic surfactant, propylene glycol, water and the like.

The dosage form is exemplified by tablet, capsule, granule, powder, syrup, suspension, ointment, gel, patch, injection, eye drop and the like. These preparations can be prepared according to a conventional method appropriately using the above carrier for preparation. In the case of a liquid preparation, it may take the form involving dissolving or suspending in water or other suitable medium when in use. It is also possible to apply coating to tablet and granule by a well-known method.

The administration route of the agent or pharmaceutical composition for the prophylaxis or treatment of diabetic neuropathy of the present invention may be any and is selected depending on the dosage form thereof from oral administration, parenteral administration, intrarectal administration and local administration.

While the dose of CDP-choline, which is an active ingredient of the agent or pharmaceutical composition for the prophylaxis or treatment of diabetic neuropathy of the present invention, varies depending on the administration method, symptom and age of patient, and the like, it is generally about 0.1–1000 mg/kg/day, preferably about 0.5–500 mg/kg/day, which can be administered in a single dose or divided doses.

The agent or pharmaceutical composition for the prophylaxis or treatment of diabetic neuropathy of the present invention may contain other ingredients effective for the treatment of diabetes, such as oral hypoglycemic agent and the like. The agent or pharmaceutical composition for the prophylaxis or treatment of diabetic neuropathy of the present invention can be administered in combination with a hypoglycemic agent (e.g., insulin, gliclazide, glibenclamide, tolbutamide, acetohexamide and the like).

EXAMPLES

The present invention is explained in detail by referring to Examples and Formulation Examples, which are not to be construed as limitative.

Example 1

Effect of CDP-choline on Diabetic Peripheral Neuropathy (1)

Test compound: cytidine 5'-diphosphocholine monosodium salt (CDP-choline Na: manufactured by Yamasa Corporation)
Test: assessment (threshold analysis) of thermal nociceptive response using diabetic mouse (in vivo)
This test was performed according to the method of Osawa and Kamei [Eur. J. Pharmacol., 372, 221 –228 (1999)].
(1) Preparation of Diabetic Mouse
Streptozotocin (200 mg/kg) dissolved in citrate buffer (pH 4.5) was administered into the tail vein of male ICR mice (10 per group, body weight: about 20 g) to induce diabetes.
(2) Administration of CDP-choline
CDP-choline Na was dissolved in distilled water and orally administered at a dose of 100 mg/kg once a day from immediately after induction of diabetes.

(3) Assessment (threshold analysis) of Thermal Nociceptive Response

The assessment was performed using a tail-flick test. To be specific, photothermic stimulation was given to the tail of mouse, and the reaction latency until it moves the tail feeling the heat was measured. How the reaction latency changed in the diabetes group as compared tot he normal group and the results with administration of 100 mg/kg of CDP-choline to the diabetes group are shown in FIG. 1.

As is evident from this Figure, the reaction latency was significantly shortened in the early stages of disease (between 1 and 4 weeks) in the diabetes group as compared to the normal group, exhibiting a symptom (hyperlagesia) similar to allodynia observed in diabetic human patients. A significant prolongation of the reaction latency was observed from 6 weeks, and diminished sensation of sensory nerve as in diabetic human patients was observed.

When 100 mg/kg of CDP-choline was administered to the diabetes group showing the conflicting biphasic neuropathy observed with the lapse of time, the above neuropathy was almost completely inhibited, and the reaction latency shifted at the same level as in the normal group. In the Figure, the measures show mean±S.E. of reaction latency of 10 mice, wherein * shows a significant difference (P<0.05) from the normal group, and # shows a significant difference (P<0.05) from the diabetes group.

The results have revealed that oral administration of CDP-choline prior to the onset of symptoms specific to diabetic peripheral neuropathy showing a diversity of symptoms affords inhibition of the onset of the symptoms.

When the dose of CDP-choline was set to 300 mg/kg, a similar effect was found. It had already been confirmed that administration of 100 or 300 mg/kg of CDP-choline to the normal group has no effect on the reaction latency.

Example 2

Effect of CDP-choline on Diabetic Peripheral Neuropathy (2)

Figure 2:
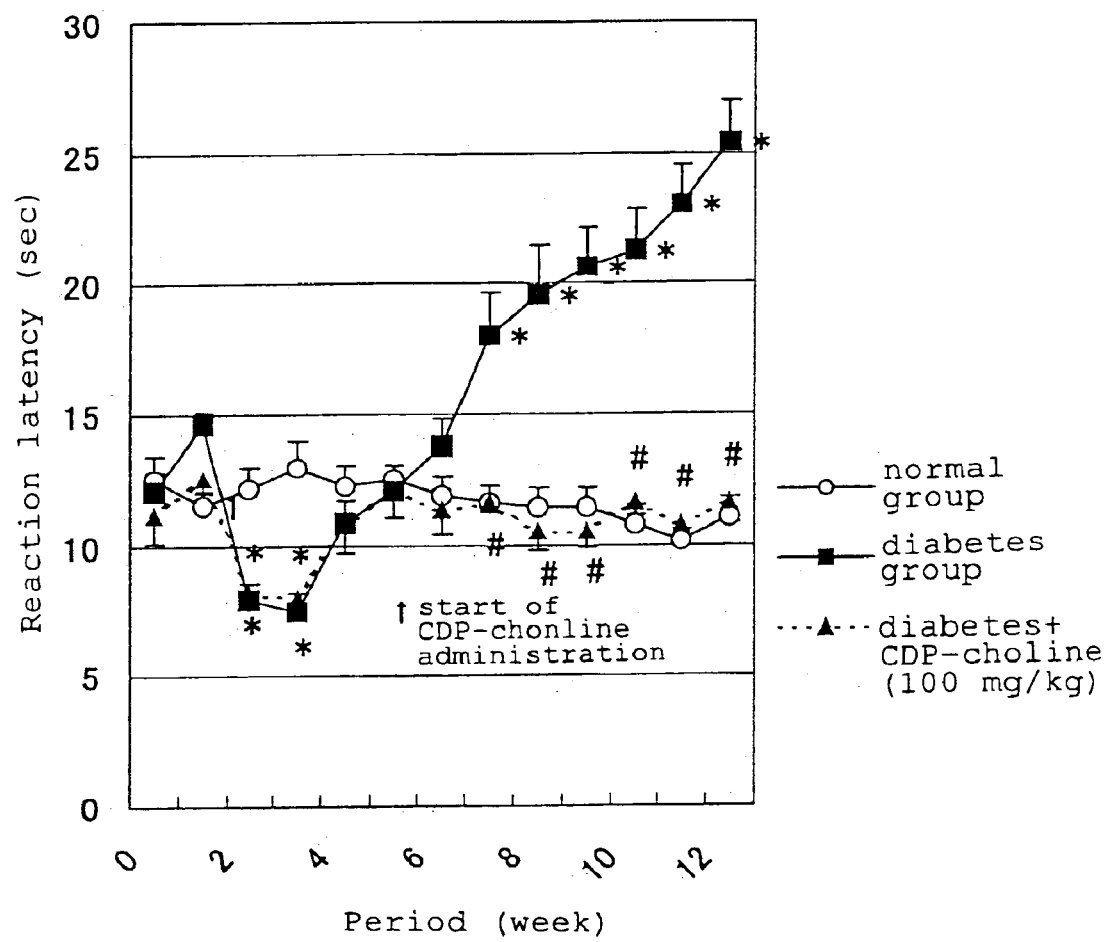
FIG. 2 shows the results of CDP-choline regarding assessment (threshold analysis) of thermal nociceptive response, wherein the longitudinal axis shows reaction latency (sec) and the transverse axis shows period after diabetes have been induced.

Test compound: CDP-choline Na
Test assessment (threshold analysis) of thermal nociceptive response using diabetic mouse (in vivo) (see the method of Osawa and Kamei [Eur. J. Pharmacol., 372, 221–228 (1999)])
(1) Preparation of Diabetic Mouse
Streptozotocin (200 mg/kg) dissolved in citrate buffer (pH 4.5), was administered into the tail vein of male ICR mice (12–13 per group, body weight: about 20 g) to induce diabetes.
(2) Administration of CDP-choline
CDP-choline Na was dissolved in distilled water and orally administered at a dose of 100 mg/kg once a day starting from the time point when 5 weeks passed from the administration of streptozotocin.
(3) Assessment (Threshold Analysis) of Thermal Nociceptive Response The assessment was performed using a tail-flick test. The results are shown in FIG. 2. As shown in this Figure, in the case of administration of CDP-choline (100 mg/kg) to the diabetes group was started from the 5 weeks post-streptozotocin, prolongation of the reaction latency, namely diminished sensation of the sensory nerves was almost completely inhibited, and the reaction latency shifted at the same level as in the normal group. In the Figure, the measures show mean±S.E. of the reaction latency of 12–13 mice, wherein * shows a significant difference (P<0.05) from the normal group, and # shows a significant difference (P<0.05) from the diabetes group.

The results have revealed that oral administration of CDP-choline even after the onset of symptoms specific to diabetic neuropathy showing a diversity of symptoms affords inhibition of the symptoms.

While the data are not shown this time, a similar effect was observed when the dose of CDP-choline was set to 30 mg/kg.

Example 3

Effect of CDP-choline on Diabetic Peripheral Neuropathy (3)

Test Compound: CDP-choline Na
Test: assessment (threshold analysis) of thermal nociceptive response using diabetic mice (in vivo) (see the method of Osawa and. Kamei [Eur. J. Pharmacol., 372, 221–228 (1999)])
(1) Preparation of Diabetic Mouse
Streptozotocin (200 mg/kg) dissolved in citrate buffer (pH 4.5) was administered into the tail vein of male ICR mice (10 per group, body weight: about 20 g) to induce diabetes.
(2) Administration of CDP-choline
CDP-choline Na was dissolved in distilled water and orally administered at a dose of 100 mg/kg once a day starting from the time point when 8 weeks passed from the administration of streptozotocin.
(3) Assessment (Threshold Analysis) of Thermal Nociceptive Response
The assessment was performed using a tail-flick test. As a result, the reaction latency was prolonged in the diabetes group with the lapse of time from the time point when 8 weeks passed from the administration of streptozotocin, but prolongation of the reaction latency, or further aggravation of diminished sensation of sensory nerves, was not observed in the CDP-choline 100 mg/kg administration group, and a significant reaction latency prolongation-inhibitory effect was observed at the lapse of 11 weeks after the administration of streptozotocin.

Example 4

Effect of CDP-choline on Diabetic Dysautonomia

Test compound: CDP-choline Na
Test: Charcoal powder transportability test of gastrointestinal tract using diabetic mice (in vivo)
(1) Preparation of Diabetic Mouse
Streptozotocin (200 mg/kg) dissolved in citrate buffer (pH 4.5) was intraperitoneally administered to male ICR mice (7–11 per group, body weight: about 20 g) to induce diabetes.
(2) Administration of CDP-choline
CDP-choline Na was dissolved in distilled water and orally administered at a dose of 100 mg/kg once a day from immediately after induction of diabetes.
(3) Charcoal Powder Transportability Test of Gastrointestinal Tract
The mice that had undergone streptozotocin administration 8 weeks before were used for the test. A 5% activated charcoal powder suspension was prepared using 0.5% aqueous carboxymethylcellulose solution, and orally administered at 0.1 ml/mice to mice fasted from the previous day. After 30 min, the gastrointestinal tract from pyloric portion of stomach to rectum was enucleated and the whole length was measured. In addition, the position of the activated charcoal powder after movement was confirmed and the distance of movement from pyloric portion of stomach was measured. This was converted to numerical values based on the whole length of from pyloric portion of stomach to rectum as 100%, and the data was processed and taken to show charcoal powder transportability of gastrointestinal tract.

How the charcoal powder transportability of gastrointestinal tract changed in the diabetes group as compared to the normal group and the results with administration of 100 mg/kg of CDP-choline to the diabetes group are shown in Table 1. In Table 1, the normal group, diabetes group and diabetes+CDP-choline administration group were divided into three criteria of less than 40%, not less than 40% and less than 60%, and not less than 60% of charcoal powder transportability of gastrointestinal tract, and the number of incidents in each criterion is shown in percentage.

As is evident from this Table, not a single mouse in the normal group showed charcoal powder transportability of gastrointestinal tract of less than 40%, and the incidence of mice showing charcoal powder transportability of gastrointestinal tract of not less than 40% and less than 60% exceeded 90%. In contrast, the mice in the diabetes group showed a high incidence of 54.5% of mice that showed charcoal powder transportability of gastrointestinal tract of less than 40%, indicating more markedly degraded charcoal powder transportability of gastrointestinal tract than in the normal group.

The functional degradation of charcoal powder transportability of gastrointestinal tract highly frequently found in the diabetes group is caused by dysautonomia. In the group that was given 100 mg/kg of CDP-choline for such disorder, not a single mouse showed charcoal powder transportability of gastrointestinal tract of less than 40%, thus showing complete inhibition of degradation of charcoal powder transportability of gastrointestinal tract highly frequently found in the diabetes group.

From these results, it has been clarified that oral administration of CDP-choline affords inhibition of the onset of or amelioration of the symptoms specific to diabetic dysautonomia, such as degradation of charcoal powder transportability of gastrointestinal tract and the like.

TABLE 1

| | Charcoal powder transportability of gastrointestinal tract | | |
|---|---|---|---|
| | less than 40% | not less than 40% and less than 60% | not less than 60% |
| normal group (%) | 0 | 90.9 | 9.1 |
| diabetes group (%) | 54.5 | 27.3 | 18.2 |
| Diabetes + CDP-choline administration group (%) | 0 | 71.4 | 28.6 |

Example 5

Effect of Related Compounds on Diabetic Peripheral Neuropathy

Test compound 1: CDP-choline Na
  Dose 100 mg/kg ($1.959 \times 10^{-4}$ mol/kg)
Test compound 2: triacetyluridine
  Dose 100 mg/kg ($2.7 \times 10^{-4}$ mol/kg)
Test compound 3: cytidine
  Dose 100 mg/kg ($4.111 \times 10^{-4}$ mol/kg)
Test compound 4: cytidine 5'-monophosphate disodium salt (5'-CMP 2Na)
  Dose 100 mg/kg. ($2.723 \times 10^{-4}$ mol/kg)
Test compound 5: phosphorylcholine chloride, calcium salt (P-choline)
  Dose: 100 mg/kg ($3.88 \times 10^{-4}$ mol/kg)

Test compound 6: cytidine 5'-monophosphate disodium salt (5'-CMP 2Na)+phosphorylcholine chloride, calcium salt (P-choline)

Dose: 72 mg/kg ($1.959 \times 10^{-4}$ mol/kg) as 5'-CMP 2Na and 50.5 mg/kg ($1.959 \times 10^{-4}$ mol/kg) as P-choline Test: assessment (threshold analysis) of thermal nociceptive response using diabetic mouse (in vivo) (see the method of Osawa and Kamei [Eur. J. Pharmacol., 372, 221–228 (1999)])

(1) Preparation of Diabetic Mouse

Streptozotocin (200 mg/kg) dissolved in citrate buffer (pH 4.5) was administered into the tail vein of male ICR mice (12–13 per group, body weight: about 20 g) to induce diabetes.

(2) Administration of Test Compound

Test compounds were dissolved in distilled water or suspended in 0.5% aqueous carboxymethylcellulose solution and orally administered once a day starting from the time point when 5 weeks passed from the administration of streptozotocin.

(3) Assessment (Threshold Analysis) of Thermal Nociceptive response

Figure 3:
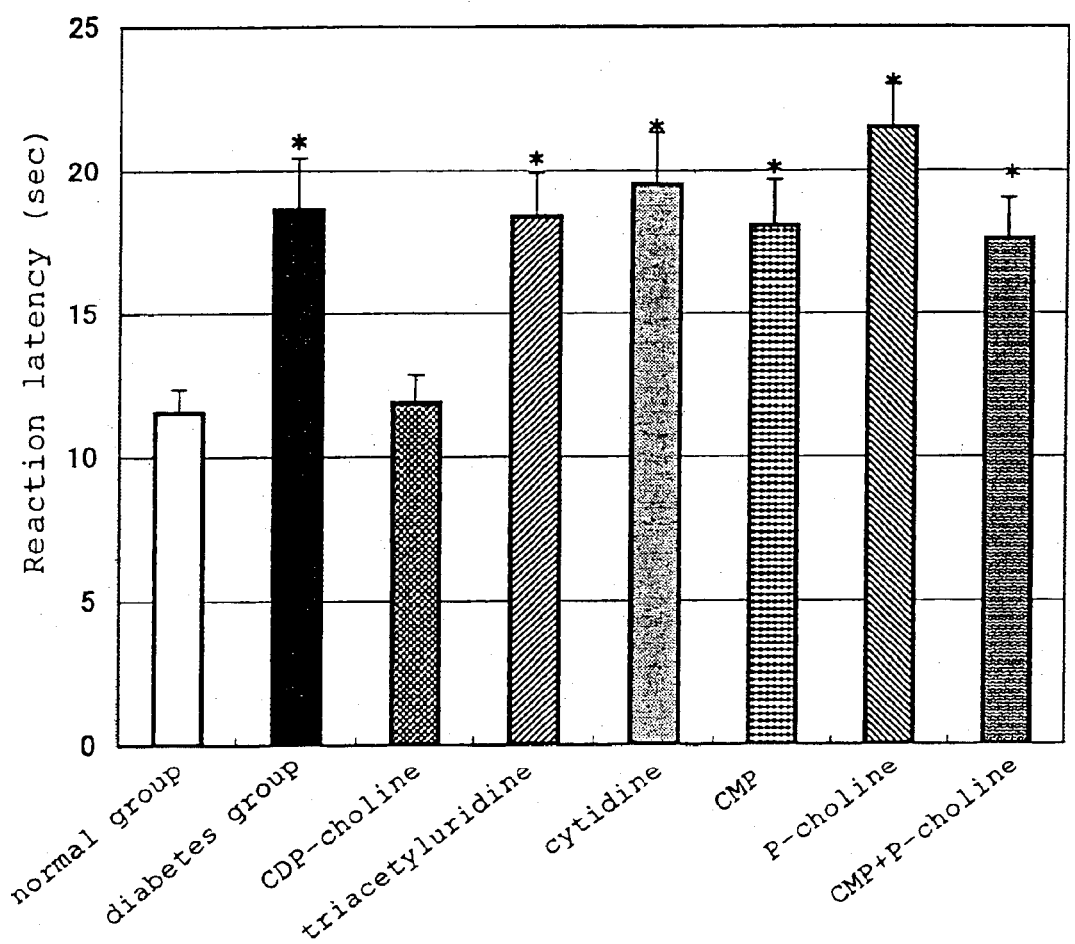
FIG. 3 shows the results of CDP-choline and related compounds regarding assessment (threshold analysis) of thermal nociceptive response, wherein the longitudinal axis shows reaction latency (sec).

The assessment was performed using a tail-flick test. As a result, the reaction latency was significantly prolonged in the diabetes group from the time point when 6 weeks passed from the streptozotocin administration, and diminished sensation of sensory nerve as in diabetic human patients was observed. When administration of CDP-choline (100 mg/kg) to the diabetes group was started from the 5 weeks post-streptozotocin, prolongation of the reaction latency, namely diminished sensation of the sensory nerves, was nearly completely inhibited, and the reaction latency was of the same level as in the normal group. In other test compound (including triacetyluridine) administration group, however, significant prolongation of the reaction latency as in the diabetes group was found, and an inhibitory effect on diminished sensation of the sensory nerves as afforded by CDP-choline was not observed. As typical data thereof, the data on lapse of 7 weeks after the streptozotocin administration are shown in FIG. 3. In the Figure, the measures show mean±S.E. of the reaction latency of 12–13 mice, wherein * shows a significant difference ($P<0.01$) from the normal group.

It was also confirmed that data showing similar tendency as does the results at 7 weeks are obtained on lapse of 6 or 8 weeks after the streptozotocin administration.

It has been reported that oral administration of CDP-choline results in almost the same level of bioavailability as by intravenous administration [Methods Find. Exp. Clin. Pharmacol. 17, Suppl. B, 1–15, (1995)], and combined with the above results showing no efficiency of the related compounds, it is inferred that the CDP-choline itself is an active principle.

Preparation Example 1

Tablet

| | |
|---|---|
| CDP-choline | 30.0 mg |
| fine powdered cellulose | 25.0 mg |
| lactose | 39.5 mg |
| starch | 40.0 mg |
| talc | 5.0 mg |
| magnesium stearate | 0.5 mg |

Tablets are prepared from the above composition by a conventional method.

Preparation Example 2

Capsule

| | |
|---|---|
| CDP-choline | 30.0 mg |
| lactose | 40.0 mg |
| starch | 15.0 mg |
| talc | 5.0 mg |

Capsules are prepared from the above composition by a conventional method.

Preparation Example 3

Injection

| | |
|---|---|
| CDP-choline | 30.0 mg |
| glucose | 100.0 mg |

The above composition is dissolved in purified water for injection to prepare injection.

INDUSTRIAL APPLICABILITY

The agent or pharmaceutical composition for the prophylaxis or treatment of diabetic neuropathy of the present invention containing CDP-choline as an active ingredient inhibits the onset of symptoms specific to diabetic neuropathy such as diabetic peripheral neuropathy and diabetic dysautonomia, and further shows a potent improving effect even after the onset thereof and is superior in safety. Consequently, it can be used for the prophylaxis or treatment of neuropathy as a therapeutic drug for diabetic complications. Moreover, because it shows effect by oral administration, it is also effective for improving QOL (Quality of Life) of patients.

This application is based on a patent application Ser. Nos. 2001-268156 and 2001-340838 filed in Japan, the contents of which are hereby incorporated by reference.

The references cited herein, including patent applications, are hereby incorporated in their entireties by reference, to the extent that they have been disclosed herein.

What is claimed is:

1. A method for treatment of diabetic neuropathy, which comprises administering an effective amount of cytidine 5'-diphosphocholine or a pharmaceutically acceptable salt thereof to a patient in need thereof.

2. The method of claim 1, wherein the diabetic neuropathy is a neuropathy mainly caused by metabolic disturbance of a carbohydrate.

3. The method of claim 1, wherein the diabetic neuropathy is peripheral neuropathy.

4. The method of claim 1, wherein the diabetic neuropathy is dysautonomia.

5. The method of claim 1, which comprises oral administration.

* * * * *